(12) United States Patent
Mensah

(10) Patent No.: US 6,544,513 B2
(45) Date of Patent: *Apr. 8, 2003

(54) METHOD OF CONTROLLING MOTH AND OTHER INSECT PESTS

(75) Inventor: Robert Kofi Mensah, Orange (AU)

(73) Assignee: The State of New South Wales C/- NSW Department of Agriculture (AU)

(*) Notice: Subject to any disclaimer, the term of this patent is extended or adjusted under 35 U.S.C. 154(b) by 0 days.

This patent is subject to a terminal disclaimer.

(21) Appl. No.: 09/782,074

(22) Filed: Feb. 12, 2001

(65) Prior Publication Data

US 2001/0024646 A1 Sep. 27, 2001

Related U.S. Application Data

(63) Continuation-in-part of application No. 09/448,798, filed on Nov. 24, 1999, now Pat. No. 6,274,137, which is a continuation of application No. 08/809,522, filed as application No. PCT/AU95/00633 on Sep. 26, 1995, now abandoned.

(30) Foreign Application Priority Data

Sep. 26, 1994 (AU) .............................. PM8407

(51) Int. Cl.$^7$ ................................ A01N 63/00
(52) U.S. Cl. .................. 424/93.51; 424/115; 424/405; 504/117
(58) Field of Search .............. 424/93.51, 115, 424/405; 504/117

(56) References Cited

U.S. PATENT DOCUMENTS

| 4,598,862 A | 7/1986 | Rice ............................ 239/8 |
| 4,599,362 A | 7/1986 | Nakatani et al. ............ 514/721 |

FOREIGN PATENT DOCUMENTS

| CA | 1185172 | 4/1985 |
| DE | 4005628 | 7/1980 |
| EP | 0462347 | 12/1991 |
| EP | 0563963 | 10/1993 |
| JP | 52082728 | 7/1977 |
| JP | 52099217 | 8/1977 |
| JP | 54132237 | 10/1979 |
| JP | 59128317 | 7/1984 |
| SU | 745944 | 7/1980 |
| WO | 91/19417 | 12/1991 |

OTHER PUBLICATIONS

Smith et al., Queensland Journal of Agricultural and Animal Sciences, 45(2):169–177, Dec. 1988.

Pristavko et al., Entomol. Rev., Oct./Dec. 1974 (transl. 1975) 53(4):28–34.

Gillott, Entomology, 1995, Plenum Press, pp. 691–702, 723–730 & 739.

*Primary Examiner*—Irene Marx
(74) *Attorney, Agent, or Firm*—Ostrolenk, Faber, Gerb & Soffen, LLP

(57) ABSTRACT

A method of controlling various insect pests on a plant is disclosed which consists of attracting, augmenting or conserving natural enemies of the insect pests in order to produce a population of the natural enemies sufficient to control the insect pest by applying to the plant an effective amount of a brewer's yeast, *S. cerevisiae* YESTA 20B (a dried debittered brewer's yeast).

7 Claims, 7 Drawing Sheets

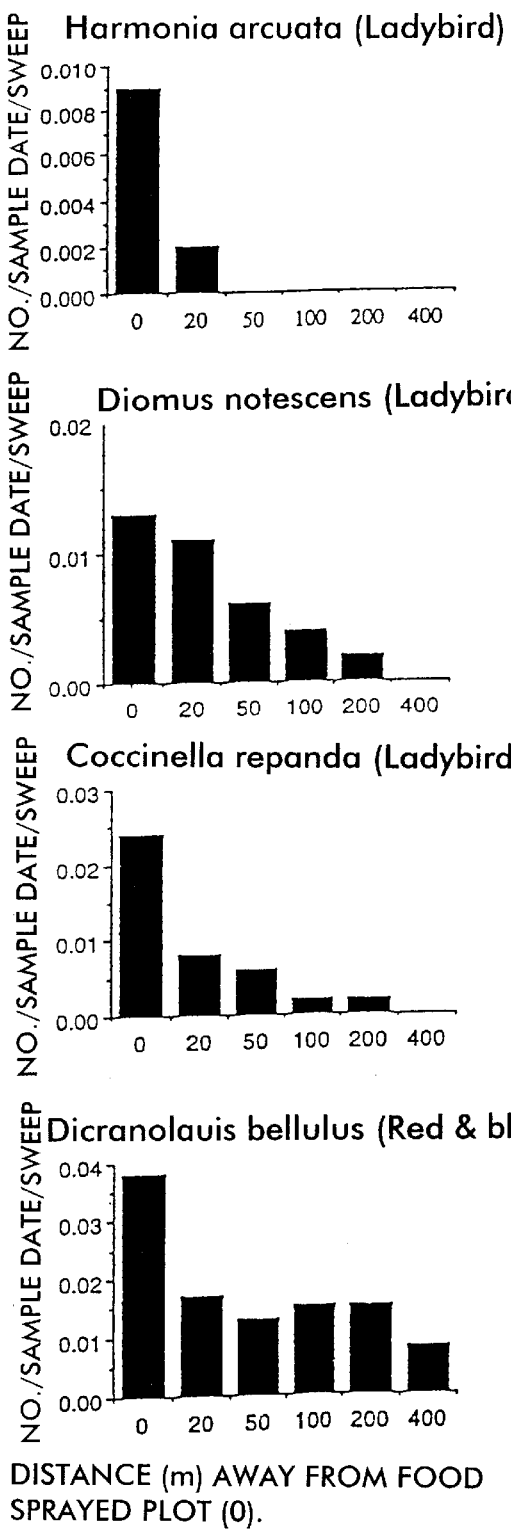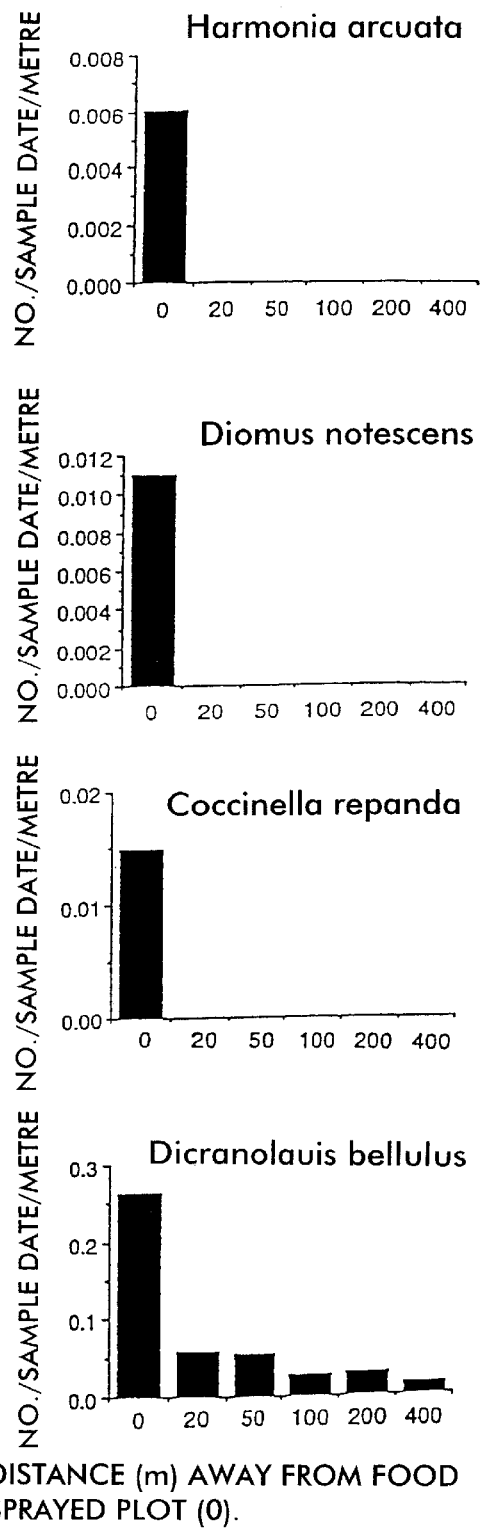
FIG. 2a
FIG. 2b

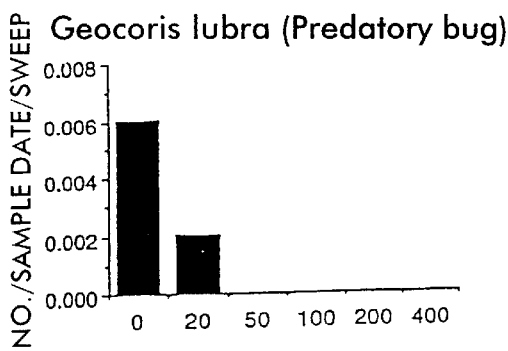
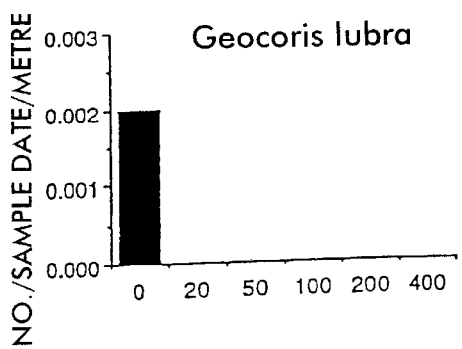
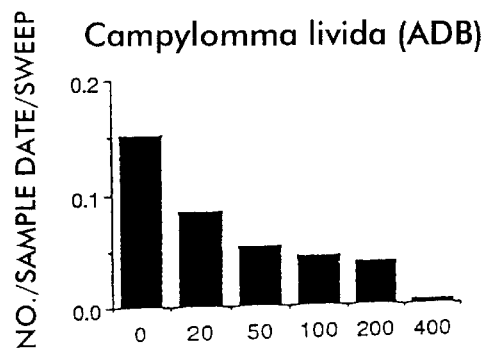
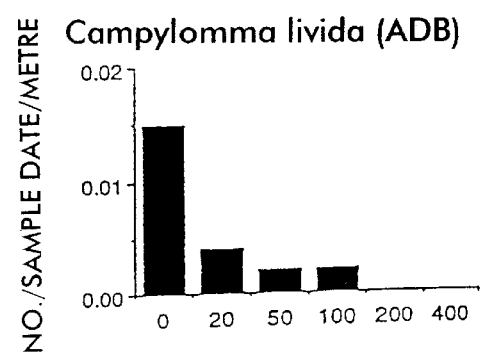
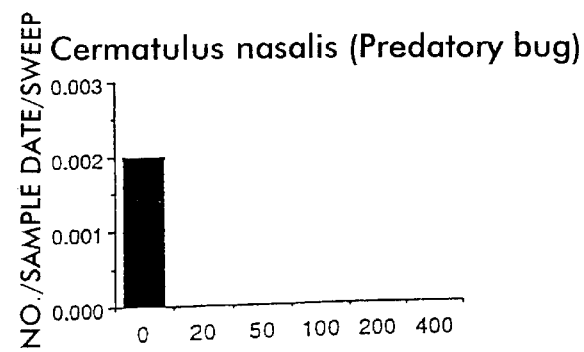
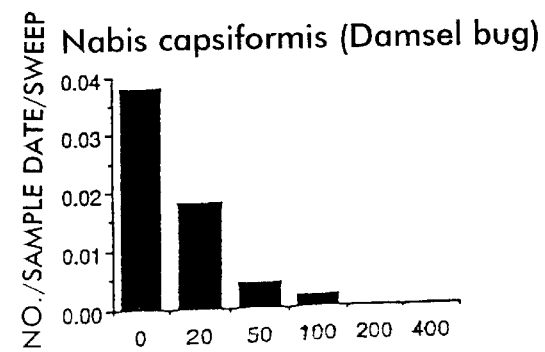
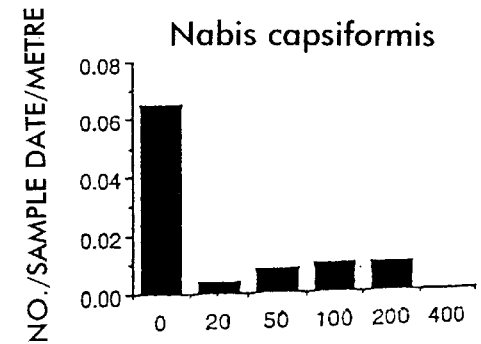
DISTANCE (m) AWAY FROM FOOD SPRAYED PLOT (0).
FIG. 3a
DISTANCE (m) AWAY FROM FOOD SPRAYED PLOT (0).
FIG. 3b

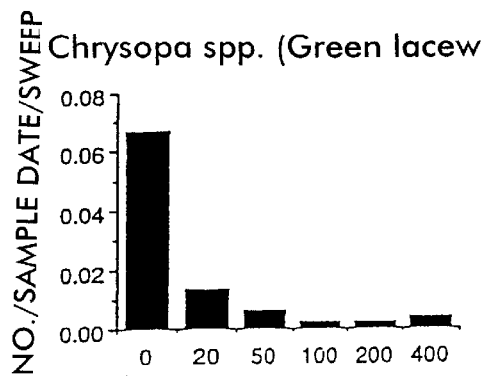
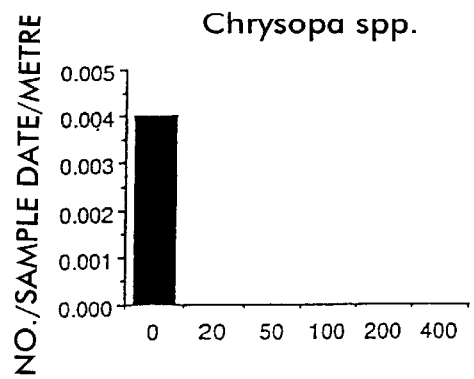
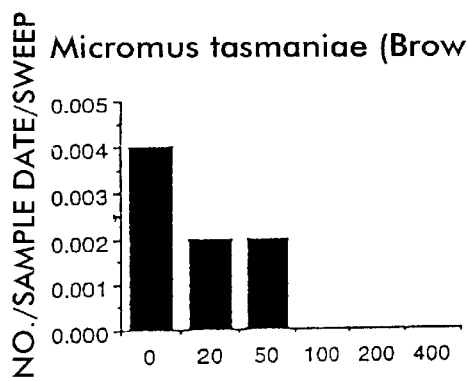
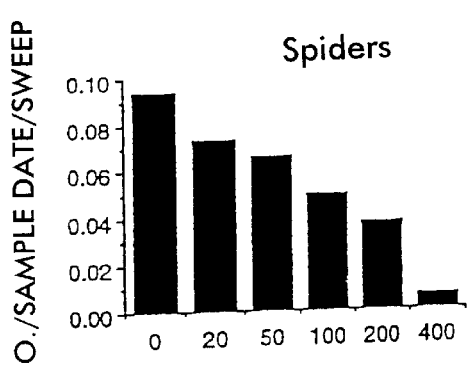
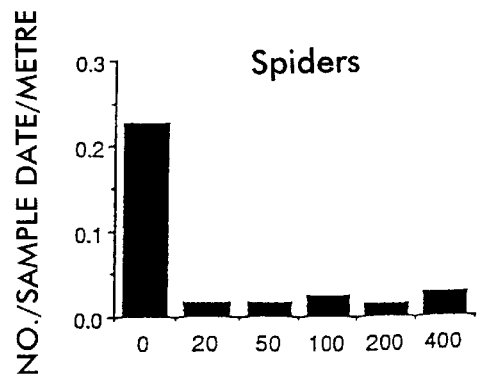
DISTANCE (m) AWAY FROM FOOD SPRAYED PLOT (0).
DISTANCE (m) AWAY FROM FOOD SPRAYED PLOT (0).
FIG. 4a
FIG. 4b

METHOD OF CONTROLLING MOTH AND OTHER INSECT PESTS

CROSS-REFERENCES TO RELATED APPLICATIONS

This application is a continuation-in-part of U.S. Ser. No. 09/448,798, filed Nov. 24, 1999, now U.S. Pat. No. 6,274, 137, issued Aug. 14, 2001, which is a continuation of application Ser. No. 08/809,522, filed Mar. 26, 1997, which is a national stage application of PCT International Application No. PCT/AU95/00633, filed Sep. 26, 1995, claiming priority of Australian Application No. PM 8407, filed Sep. 26, 1994.

BACKGROUND OF THE INVENTION

1. Field of the Invention

This invention relates to the use of yeast for the control of moth of other insect pests and for attracting and conserving predatory insects of the pests. In particular, the present invention relates to the use of yeast for the control of cotton bollworm and native budworm.

2. Description of the Related Art

Cotton bollworm (*Helicoverpa armigera* Hubner) and native bud worm (*Helicoverpa punctigera* Wallengren) are the major pests of cotton. Both insects are polyphagous and they feed preferentially on young growing tips or reproductive structures. The adults feed on nectar and the damage they cause is the result of the larvae feeding on leaves and buds or bolls. Infestations of these moths results in the loss of the terminal bud or fruiting structures either as floral buds (squares) or as fruit (bolls) causing considerable yield loss. Host plants other than cotton include maize, sorghum, wheat, sunflower, lucerne, various legumes especially soybean, pigeon pea and chickpea, tomatoes, okra, other vegetables, fruits, top fruits and citrus.

*H. armigera* is cosmopolitan and is the principal species in the Old World from Africa to the Pacific Islands but *H. punctigera* is an endemic species. Infestation of cotton by Helicoverpa spp. may occur at anytime after seedling emergence, but their abundance is highly variable being influenced by environmental factors, natural enemy abundance, quality and quantity of host plants and also their migratory movements. The two species usually follow a regular pattern of abundance in all areas they attack with *H. punctigera* the dominant species prior to flowering and well into summer (January). *H. armigera* becomes dominant from January onwards in most areas and is rarely seen in early season cotton.

The current control programme for cotton bollworm and native budworm in cotton relies heavily on synthetic insecticides. Cotton crops receive on average 12 insecticide and insecticide mixture sprays each season, although extremes of 18–20 sprays still occur. In 1991 Australian cotton growers spent approximately A$74 million on insecticides, A$15 million on application costs and A$9 million for professional consultants giving total insect control costs approaching A$100 million per year. The over-reliance on insecticides and its associated problems of insecticide resistance especially in *H. armigera*, disruption of natural enemies of the pests and environmental consequences due to residues in soil and water, off-target drift near human habitation have cast doubt on the long term viability of the cotton industry and the classical insecticide approach. It is therefore essential that an alternative non-chemical control measure be developed against the pest to achieve sustainability of cotton production.

Presently with our monoculture practices in agriculture and the use of pesticides we are inadvertently discriminating against beneficial insects. Many areas where crops are grown especially cotton growing areas are remote from wild vegetation. They are often treeless, bushless, reckless and often lay fallow most part of the year. With no natural refuges, no food sources for adult natural enemies of phytophagous insects, beneficial insects are made ineffective. There is therefore lack of diversity and instability in the agroecosystem.

BRIEF SUMMARY OF THE INVENTION

The present invention relates to a method of controlling an insect pest selected from the group consisting of cotton bollworm, native budworm, plaque thrips, cotton bud thrips, predatory thrips, onion thrips, *Earias huegeli* (Rough bollworm), *Crocidosema plebeiana* (Cotton tipworm), *Pectinophora scutigera* (Pink bollworm), *Anomis flava* (Cotton looper), *Loxostege affinitalis* (Cotton web-spinner), *Agrotis infusa* (Bogong moth), *Spodoptera litura* (Cluster caterpillar), *Chryssodeixis argentifera* (Tobacco looper), *Tetranychus urticae* (Two spotted mites), *Aphis gossypii* (Cotton aphid), *Myzus persicae* (Green peach aphid), *Creontiades dilutus* (Green mirid) and *Campylomma livida* (Apple dimpling bug) on a plant, which comprises attracting, augmenting or conserving natural enemies of the insect pest in order to produce a population of the natural enemies sufficient to control the insect pest by applying to the plant an effective amount of a brewer's yeast, *S. cerevisiae* YESTA 20B (a dried debittered brewer's yeast).

BRIEF DESCRIPTION OF THE SEVERAL VIEWS OF THE DRAWINGS

FIGS. 2a and 2b show effect of YESTA 20B (a dried debittered brewer's yeast, *S. cerevisiae*) on the abundance of predatory beetles of Helicoverpa spp. on commercial cotton at Norwood, near Moree (Results from Dec. 11, 1992 to Jan. 21, 1993 using a sweep net (a), and from Jan. 28, to Mar. 4, 1993 using a D-vac (b).

FIGS. 3a and 3b show effect of provision of YESTA 20B (a dried debittered brewer's yeast, *S. cerevisiae*) on numbers of predatory bugs of Helicoverpa spp. on commercial cotton at Norwood, near Moree (Results of sweep net catches (a) from Dec. 11, 1992 to Jan. 21, 1993, and (b) D-vac catches from Jan. 28, to Mar. 4, 1993).

FIGS. 4a and 4b show effect of YESTA 20B (a dried debittered brewer's yeast, *S. cerevisiae*) on the abundance of predatory lacewings and spiders attaching Helicoverpa spp. on commercial cotton at Norwood, near Moore (Results from Dec. 11, 1992 to Jan. 21, 1993 using a sweep net (a), and from Jan. 28, to Mar. 4, 1993 using a D-vac (b).

DETAILED DESCRIPTION OF THE INVENTION

Figure 1A:
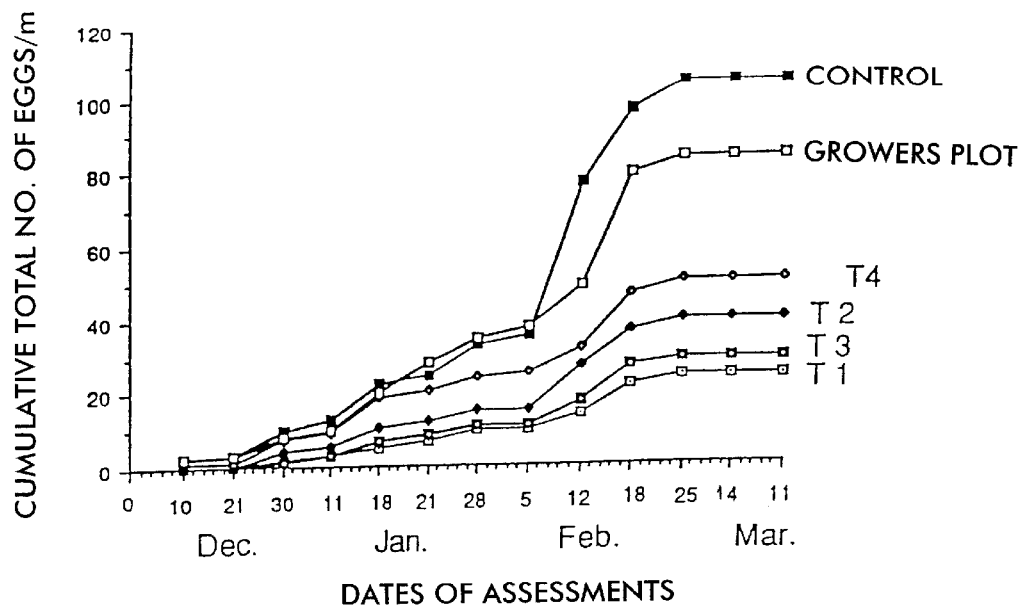
FIGS. 1a and 1b show ovipositional response of cotton boll and native bud worms to various food sprays in commercial cotton at Norwood, near Moree (a) and Auscott, Narrabri (b) during 1992/93 season. (T1=brewer's yeast (YESTA 20B); T2=sugar; T3=brewer's yeast (YESTA 20B)+sugar; T4=polysaccharide+petroleum oil).

According to the present invention there is provided a method of controlling an insect pest selected from the group consisting of cotton bollworm, native budworm, plaque thrips, cotton bud thrips, predatory thrips and onion thrips on a plant, which comprises attracting, augmenting or conserving natural enemies of the insect pest in order to produce a population of the natural enemies sufficient to control the insect pest by applying to the plant an effective amount of a dried debittered brewer's yeast, *S. cerevisiae* YESTA 20B.

The yeast of the present invention may further control insect pests through suppression and disruption of female oviposition.

Preferably, the moth or other insect pests are cotton bollworm and native budworm.

The plant may be cotton, maize, sorghum, wheat, sunflower, lucerne, various legumes especially soybean, pigeon pea and chickpea, tomatoes, okra, other vegetables, fruits, top fruits, citrus and like plants.

YESTA 20B (a dried debittered brewer's yeast, *S. cerevisiae*, a product of CPC (United Kingdom) Limited, Bovril Food Ingredients Division, Staffordshire, UK) is the yeast used, but suitable yeasts include brewer's yeast, bakers' yeast, yeast hydrolysate, and enzymatically hydrolysed yeast products, and other yeast extracts. Other suitable commercial yeast products include Feed Wheast (a product of Knudsen Creamery Company, Los Angeles, Calif., USA), Pred-Feed (a product of Custom Chemicides, Fresno, Calif.) yeast protein (Bee Wheast).

A food substance suitable for sustaining natural enemies may also be applied. This may be one or more kinds of saccharides, crude proteins, fat, fibre or ash. Other substances include natural honeydews produced by some insects, pollen from flowers, molasses, sucrose, honey, date syrup (a product of Date Factory, Tripoli, Libya) tryptophan and the like.

Preferably, the food substance is raw sugar. The yeast and raw sugar can be applied simultaneously or sequentially.

The insects that are suitable for treatment by the present invention apart from cotton bollworm and native budworm, include thrips (plague thrips, cotton bud thrips, predatory thrips, onion thrips), *Earias huegeli* (Rough bollworm), *Crocidosema plebeiana* (Cotton tipworm), *Pectinophora scutigera* (Pink bollworm), *Anomis flava* (Cotton looper), *Loxostege affinitalis* (Cotton web-spinner), *Agrotis infusa* (Bogong moth), *Spodoptera litura* (Cluster caterpillar), *Chryssodeixis argentifera* (Tobacco looper), *Tetranychus urticae* (Two spotted mites), *Aphis gossypii* (Cotton aphid), *Myzus persicae* (Green peach aphid), *Creontiades dilutus* (Green mirid) and *Campylomma livida* (Apple dimpling bug).

Natural enemies of insect pests include generalist predators and specialist parasitoids. As would be well understood by the person skilled in the art, generalist predators such as those listed in Table 6 will prey upon numerous insects including some or all of cotton bollworm, native budworm, plague thrips, cotton bud thrips, predatory thrips, onion thrips, *Earias huegeli* (Rough bollworm), *Crocidosema plebeiana* (Cotton tipworm), *Pectinophora scutigera* (Pink bollworm), *Anomis flava* (Cotton looper), *Loxostege affinitalis* (Cotton web-spinner), *Agrotis infusa* (Bogong moth), *Spodoptera litura* (Cluster caterpillar), *Chryssodeixis argentifera* (Tobacco looper), *Tetranychus urticae* (Two spotted mites), *Aphis gossypii* (Cotton aphid), *Myzus persicae* (Green peach aphid), *Creontiades dilutus* (Green mirid) and *Campylomma livida* (Apple dimpling bug) while specialist parasitoids will have a limited range of hosts among this group, for example, *P. promissorius* and *H. scaposum* parasitize cotton bollworm and native budworm. It will therefore be appreciated that attracting, augmenting or conserving such insects allows a population of natural enemies of insect pests to build up, and these natural enemies prey upon or parasitize insect pests or eat their eggs and thereby reduce numbers of insect pests. The most important generalist predators of Helicoverpa spp. are given in Table 6. Additional natural enemies of the insect pests of the present invention (which prey upon or parasitize said insect pests) include *Harmonia arcuata* Fabricuis, *Diomus notescens* Blackburn, *Coccinella repanda* Thunberg; *Campylomma livida* Reuter (predatory bugs); *Pterocormus promissorius* Erichson; *Heteropelma scaposum* Morley *Netelia producta* (Brulle) (parasitoids); *Archaearanea veruculata* Urquhart, Oxyopes spp. and Diaea spp.

Attraction and concentration of predatory insects enhances biological control of insect pests as is well known in the art. Apart from attracting and concentrating predatory insects, the yeast of the invention also increases the consumption rate of some predators, particularly ladybird beetles.

It is desirable to incorporate the activity of beneficial insects into pest management decisions. This can be achieved through the use of a predator-to-pest ratio. The application of the yeast of the present invention on commercial cotton crops can mediate changes in the predator-to-pest ratio by:

(1) attraction of predatory insects to the area by volatile compounds emitted from the yeast;

(2) arrestment of predatory insects in the area following contact and subsequent feeding on the yeast;

(3) increased searching activity induced by contact with and feeding upon the yeast;

(4) increased consumption rate of predators; and (5) decreased oviposition activity of pests such as those of Helicoverpa spp.

The present invention is also suitable for integrating with chemical treatments and/or biological treatments against the relevant pest. Suitable chemical treatments include the use of insecticides such as organochlorines (eg endosulfan, dicofol), organophosphates (eg accephate Chlorpyrifos, demeton-s-methyl, dimethoate, disulfoton, formothion, monocrotophos, omethoate, parathionmethyl, phorate, profenofos, sulprofos, thiometon), carbamates (aldicarb, carbaryl, methomyl, thiodicarb), pyretroids alphamethrin, beta-cyfluthrin, deltamethrin, esfenvalerate, fenvalerate fluvalinate, lambda-cyhalothrin), chitin inhibitors (eg chlorfluazuron), synergists (eg piperonyl butoxide (PBO), petroleum spray oil and the like. Suitable biological pesticides include *Bacillus thuringiensis* and Neem tree (*Azadiracta indica*) extracts which are known to suppress larval feeding of both cotton bollworm and native budworm.

The present invention is also suitable for combining with other treatments in order to prevent build up of resistance by the pests. The other treatment can be applied simultaneously or sequentially. For example, for a sequential treatment with a particular treatment regime for the present invention, if the regime requires treatment every fortnight, then another treatment can be used every alternate fortnight to prevent the pests from building up resistance to the present treatment. Typically, the present treatment is alternated with another treatment which includes a substance such as petroleum spray oil or a combination of petroleum spray oil and saccharides.

Suitable petroleum spray oils are white oils or dormant or summer spray oils as known in the horticultural industry. These are typically $C_{19}$–$C_{28}$ hydrocarbons. Preferably, the petroleum spray oils are $C_{19}$–$C_{21}$ but other hydrocarbons having acceptable phytotoxicity may be used. There are a number of such products on the market which are suitable for use in the present invention. These are Sunspray Ultrafine (USA EPA Reg. No. 862-23, Sunspray 6E Plus), and Sunspray 6 (USA EPA No. 862-11) and 7 (USA EPA No. 862-8), manufactured by the Sun Refining and Marketing Company, Philadelphia, Pa., USA; Caltex Lo-Vis, marketed by Caltex Oil (Australia) Pty Limited, Sydney and Ampol D-C-Tron and Ampol D-C-Tron NR, marketed by Ampol Limited, Sydney.

The petroleum spray oil and/or polysaccharide may be used in conjunction with suitable agronomically acceptable diluents and/or carriers and with other additives common in the art such as emulsifiers, wetting agents, surfactants stabilizers, spreaders or the like. A suitable additive for use in the present invention is Agral which is a nonylphenylethyleneoxide and is a non-ionic organic surfactant sold by ICI.

A typical formulation of yeast extract of the present invention comprises 1.5 kg of yeast in 20 liters of water for application per hectare.

A typical formulation of protein hydrolysate of brewer's yeast and sugar comprises of 1.5 kg of brewer's yeast+1 kg of sugar in 20 liters of water per hectare. Typically, for good crop coverage, a formulation of 1.8 kg of brewers yeast+1 kg of sugar in 30 liters of water per hectare is suitable.

Typically, the treatment involves six sprays at fortnightly intervals.

The yeast product used in the Examples is a dried debittered brewer's yeast, *S. cerevisiae* YESTA 20B, a product of CPC (United Kingdom) Limited, Bovril Food Limited Ingredient Division, Staffordshire, UK.

EXAMPLE 1

Mesh House Study on Ovipositional Response of Cotton Bollworm and Native Budworm.

An experiment to assess the ovipositional response of *Helicoverpa armigera* (cotton bollworm) and *Helicoverpa punctigera* (native budworm) was conducted under "free" and "no" choice conditions on cotton plants in a mesh house in November 1992 and January 1993 at the Narrabri Agricultural Research Station (NARS) (30° 13'S, 149° 47'E), which is situated 25 km west of Narrabri in New South Wales. The various food supplements/sprays evaluated were (1) 0.06kg of yeast in 1 L of water, (2) 0.07 kg raw sugar in 1 L of water, (3) a mixture of 0.06 kg yeast and 0.07 kg sugar in 1 L of water, (4) a mixture of 0.08 g polysaccharide and 7 ml (0.5%) petroleum oil in 1 L of water and (5) 1 L of water (control).

The experimental plants were potted cotton plants of 0.5 m high and of Sicala VI normal leaf variety. The experiment was designed as a randomised complete block with 10 replicates of each of the above 4 treatments and a control. Each replicate comprised four plants, and each row contained one replicate of each treatment. The trial was conducted separately for cotton bollworm and native budworm in the same mesh house.

Under "free" choice conditions, for each trial, the stems and leaves of each plant were sprayed in relation to each treatment for 10 seconds on both sides using a knapsack sprayer delivering 420 ml per minute. The control plants were sprayed with water. After treatment application 110 pairs (in the case of cotton bollworm) and 100 pairs (native budworm) were introduced into the mesh house to oviposit on the treated plants. The number of eggs laid on the plants were counted daily until the adults died thus giving the total number of eggs laid per plant per treatment.

Under "no" choice conditions plants from same treatment were enclosed in cages within the mesh house so Chat insects had no other choice to select from other plants receiving different treatments. Eight pairs (cotton bollworm) and 5 pairs (native budworm) were released in each cage. The same number of males were released into the cages to ensure mating. Record was taken of the total number of eggs per plant per treatment. All the data in each experiment was subjected to analysis of variance and means were compared by Duncan's multiple range test (Zar 1984).

EXAMPLE 2

Field Studies on Helicoverpa spp. Control

Experiments were conducted on commercial cotton farms at Norwood (near Moree) and Auscott (near Narrabri) in the 1992/93 cotton season. The experimental plants at each study site were of the same age and of the normal leaf variety, Sicala VI. The treatments evaluated were (1) 7.20 kg protein hydrolysate of yeast, (2) 8.40 kg of sugar, (3) a mixture of 7.20 kg of yeast and 8.40 kg sugar, (4) 9.60 g polysaccharides and 840 ml petroleum oil, (5) control (untreated) and (6) control (growers insecticide treated plot).

Experimental plots were arranged in a randomized complete block design with 4 replicates per treatment and an untreated control. Each replicate was 6 meter wide and 100 meter long. A 10 meter wide buffer separated each replicate to minimize spray drift between treatments and controls.

Pre-treatment counts of insects were made 24 h before treatment application and post-treatment every 7 days until end of study. Foliar application of each treatment were applied on Oct. 27, 1992 at Norwood and Nov. 4, 1992 at Auscott and thereafter at fortnight intervals until the end of February, 1993 when spraying was stopped at all study areas. In all 6 sprays of each treatment were applied in each study site. Sprays were applied using a knapsack sprayer delivering 420 ml per minute. On each occasion, 120 L of spray was applied in relation to each treatment, i.e. 30 L of spray per replicate. The untreated control plants were sprayed with water and the growers plot (treated control) received 12 applications of synthetic insecticides and their mixtures by means ground rig (early season i.e. October to December) and by aircraft (mid to late season i.e. January–April). The kind of pesticide, date, rate and method of applications are shown in Table 5. The growers plot was located 400 meters away from the other 4 treatments and the untreated control.

Counts of Helicoverpa spp. (eggs and larvae) were made on 1 meter sections in each replicate i.e. 4 meters for each treatment and control plots throughout the season. At each study site, the cumulative total number of eggs and larvae per meter from each treatment and control were computed. So also was the mean number of eggs and larvae per sample date per meter.

Final fruit yield (mature+open bolls) were assessed on 1 meter sections in each replicate i.e. 4 meters for each treatment and control plots at the end of the season. All data were analysed by analysis of variance and means separated by Duncan's multiple range test (Zar 1984).

To assess the effect of artificial food (represented by treatment 1) on natural enemies of cotton bollworm and native budworm, 20 sweeps using a sweep net (from Dec. 11, 1992 to Jan. 21, 1993) and a 20 meter vacuum sampling using a D-vac (from Jan. 28, 1993 to Mar. 4, 1993) were made on cotton plants at 20 meters, 50, 100, 200, 400 meters (i.e growers plot) away from treatment 1 (which is 0 meters). This was replicated 4 times at each distance. Data was expressed as numbers per sampling date per sweep or meter at each distance away from the food sprayed plot. Analysis of variance was used to analyse the data and means were compared by Duncan's multiple range test.

The results of the ovipositional response experiments under "free" and "no" choice conditions in the mesh house are shown in Tables 1 and 2. Significant difference (P<0.05) in numbers of eggs per plant laid by cotton bollworm and native budworm were found among treatments under both "free" and "no" choice conditions in the mesh house (Table 1 and 2). Maximum numbers of eggs per plant were laid on control plants (i.e. plants sprayed with only water) and minimum numbers on plants sprayed with protein hydrolysate of yeast (treatment 1) and a mixture of yeast and raw sugar (treatment 3). A mixture of polysaccharides and petroleum oil suppressed oviposition in cotton budworm but not in cotton bollworm (Table 1 and 2).

Figure 1B:
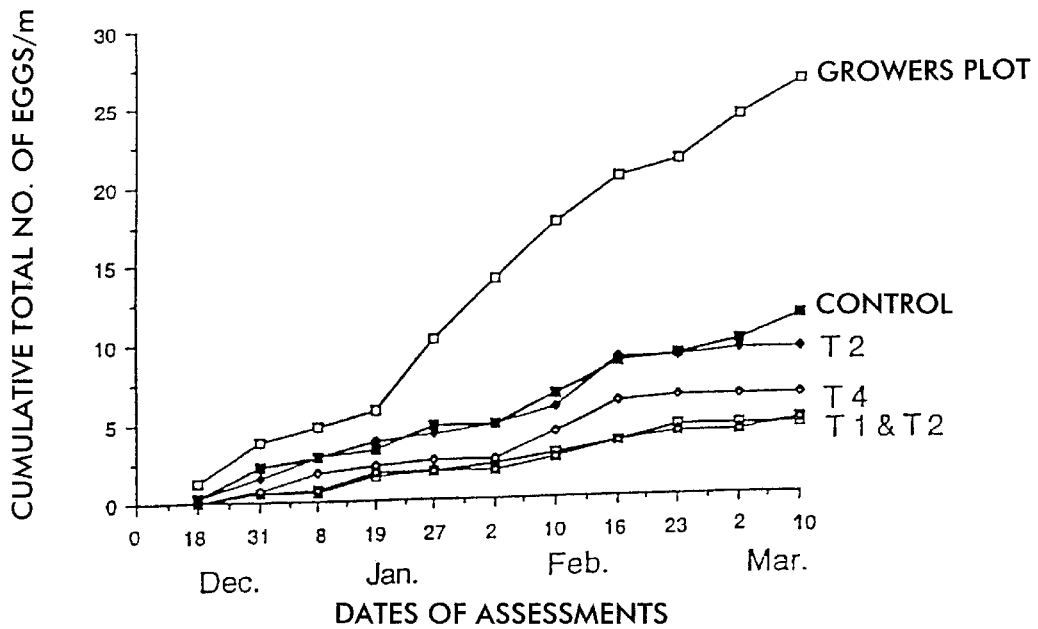

Under field conditions, oviposition of Helicoverpa spp. varied significantly (P<0.01) among treatments at both study sites (Table 3 and FIG. 1). Cotton plants which received yeast, and a mixture of yeast and sugar sprays had the least numbers of eggs laid on them compared with plants which were sprayed with either synthetic insecticide or were left unsprayed (Table 3 and FIG. 1). The higher numbers of eggs on the growers plot at both study sites indicate that the insecticides used by the growers had no ovicidal effect. Significant differences (P<0.05) in the numbers of larvae per sample date per meter were also detected among treatments only at Norwood with the growers farm recording the least numbers of larvae and that of the unsprayed plot the highest (Table 3). However there were no significant differences between the numbers of larvae per meter among the rest of the treatments. The insecticides applied by the grower at Norwood was responsible for the lower numbers of larvae on this plot. In contrast, the difference in numbers of larvae per sample date per meter among treatments at Auscott was not significantly different (P>0.05) even though the grower applied insecticides on this plot (Table 3). This was due possibly to the fact that the grower at Norwood applied more insecticides than the one at Auscott. The final fruit yield at Norwood was highest on the growers plot and also on plots which received yeast spray (treatment 1) but least on the other treatments (Table 4). In contrast the fruit yield at Auscott was highest on the yeast plot and lowest on the growers plot (Table 4). The average cost per hectare of yeast was $6.80 whereas that of the insecticides was $17 per ha in stage 1 (October–December) and $40/ha from January to March 5 when Bt was used by the grower within the insecticide resistance management programme.

Figure 5A:
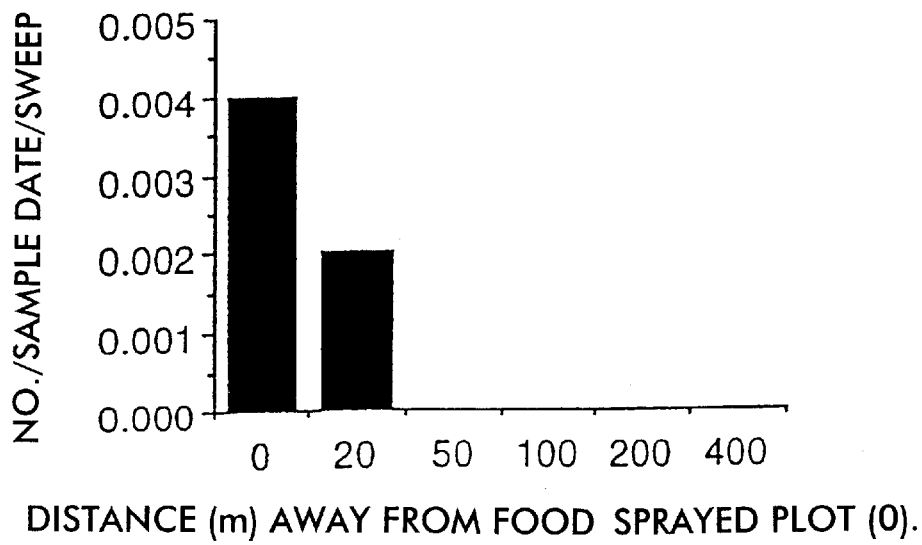
FIGS. 5a and 5b show provision of treatment with YESTA 20B (a dried debittered brewer's yeast, *S. cerevisiae*) on the abundance of some parasitoids of Helicoverpa spp. on commercial cotton at Norwood, near Moree (Results of sweep net catches).
Figure 5B:
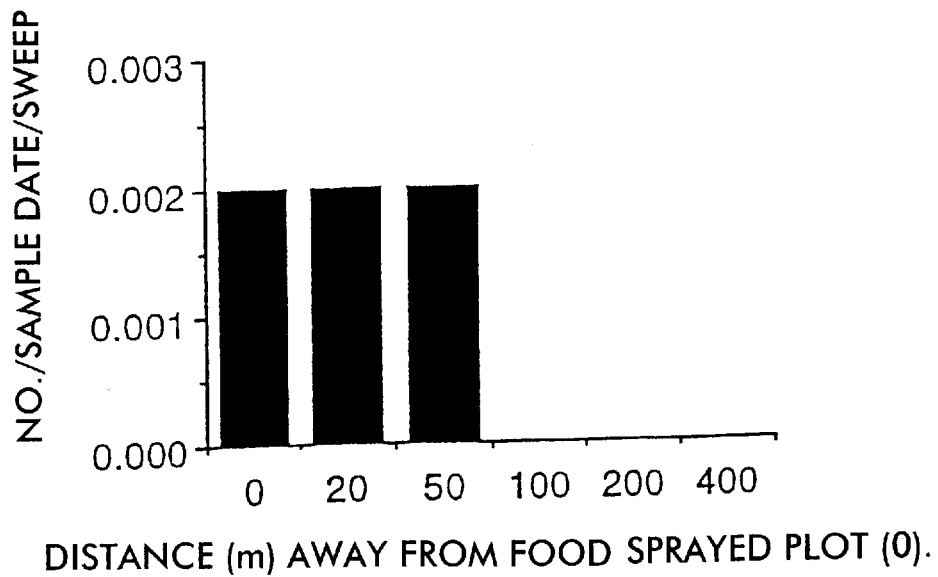

Natural enemy numbers were highest on plots receiving yeast spray (treatment 1) and continued to decline to reach its lowest level on the insecticide treated growers plot located 400 meters away (FIGS. 2, 3, 4 and 5). There was a general decline in natural enemy numbers away from the food sprayed plot (FIGS. 2–5). The natural enemies of cotton bollworm and native budworm found in high numbers in the food spray plot included the predatory beetles *H. arcuata* (three-banded ladybird), *D. notescens* (two-spotted ladybird), *C. repanda* (transverse ladybird), *D. bellulus* (red and blue beetle) (FIG. 2); predatory bugs. *G Lubra* (big-eyed bug), *C. livida* (apple dimpling bug), *C. nasalis* (glossy shield bug) and *N. capsiformis* (damsel bug) (FIG. 3); predatory lacewings Chrysopa spp. (green lacewing), *M. tasmanlae* (brown lacewing) and spiders (FIG. 4); and parasitoids of cotton bollworm and native budworm *P. promissorius* (banded caterpillar parasite) and *H. scaposum* (two-toned caterpillar parasite) (FIG. 5). Insecticides applied in the growers plot could account for lower numbers of natural enemies recorded. The higher number on the food sprayed plot indicate an attraction and conservation of the beneficial insects.

The result of the study clearly demonstrate that protein hydrolysate of yeast deters oviposition of Helicoverpa spp. females and also attracts and conserves beneficial insects of the pest in commercial cotton farms without affecting the yield of the crop. The low numbers of eggs and larvae on plots receiving yeast spray was due to a combination of oviposition suppression, predation and parasitism. The food spray resulted in fewer eggs being laid on the plot and these eggs were preyed upon by the natural enemies in this plot.

The pesticides applied to the growers plot at Norwood kept larval moth numbers low but it resulted in an outbreak of mites and aphids. None of the other treatments resulted in an outbreak of mites and aphids. There was no difference in the yields between pesticide treated plots and the yeast plots at the end of the season. Economically the food spray was cheaper and had no effect on the environment compared with insecticide spray.

EXAMPLE 3

Figure 7A:
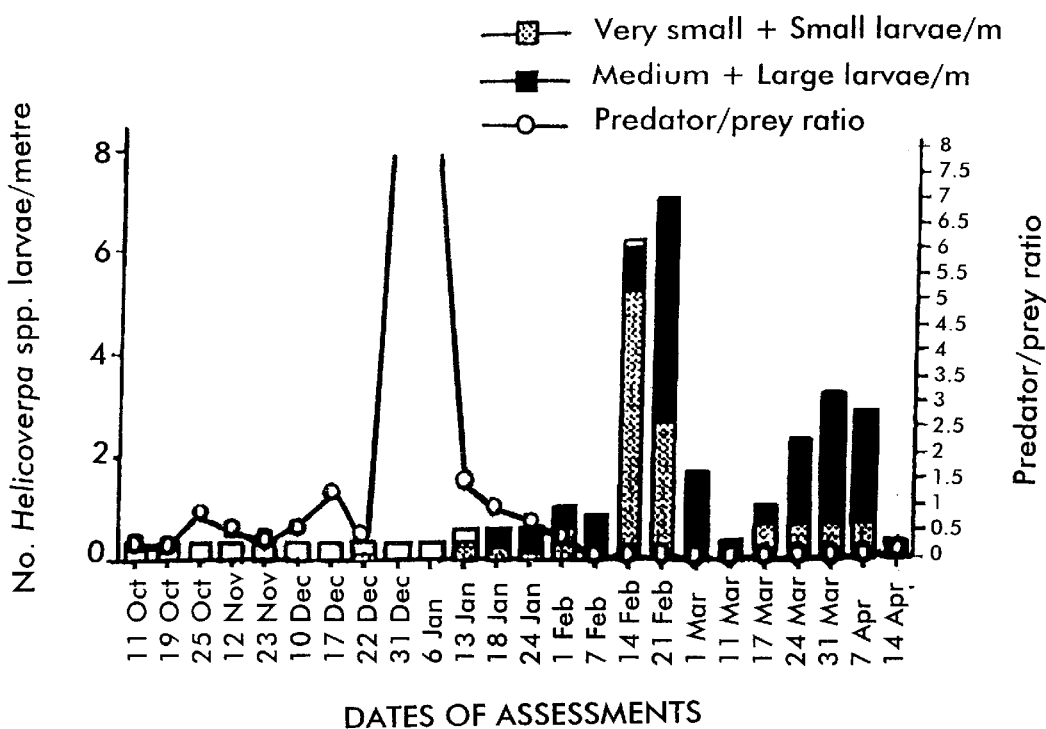
FIGS. 7*a* and 7*b* provide comparisons of predator to prey ratio on numbers of Helicoverpa spp. larvae in cotton farms at (a) Norwood in the 1993–94 season and (b) Bellevue in the 1994–95 season.
Figure 7B:
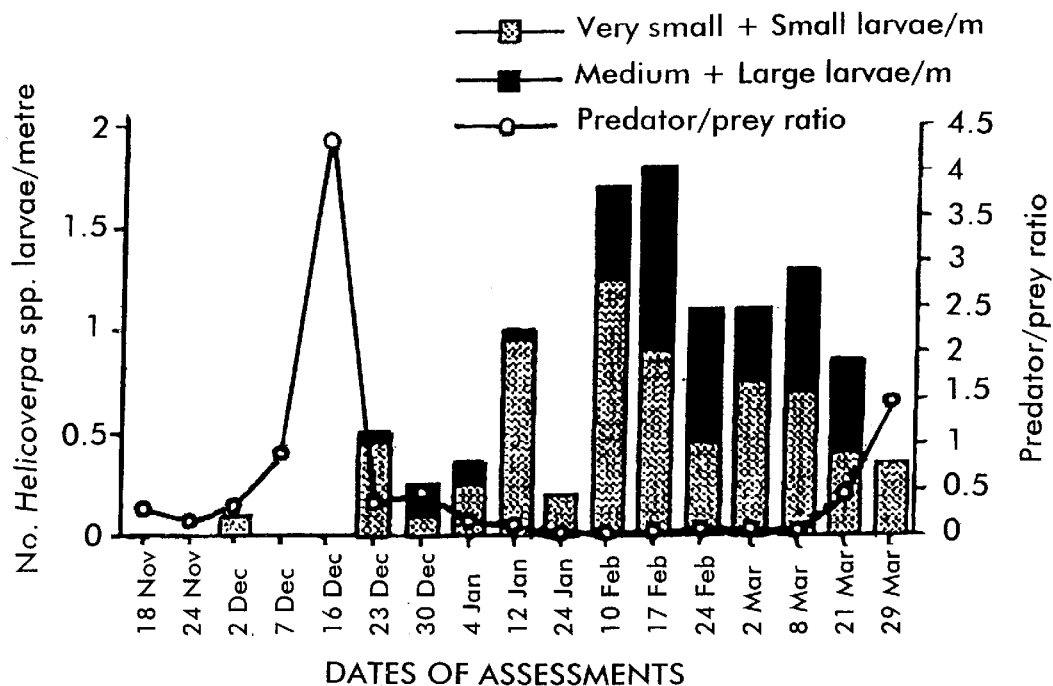

The decision to control pests such as those of Helicoverpa spp. should desirably be based on the ratio of predators to pests in the cotton crop as indicated by scouting/bug checking counts. A predator-to-pest ratio of 0.5 or higher can reduce the survival of very small larvae to medium and large larvae (FIGS. 7a and 7b). However, a ratio lower than 0.5 resulted in higher survival of Helicoverpa larvae (FIGS. 7a and 7b).

Therefore, the desired predator-to-pest threshold is 0.5 or higher.

When the predator-to-pest ratio falls below 0.5 but is higher than 0.4 and the Helicoverpa population is mostly eggs, YESTA 20B (a dried debittered brewer's yeast, *S. cerevisiae*) can be applied to attract more predators to feed on the eggs and improve the ratio.

However, when the Helicoverpa population falls below 0.5 but is higher than 0.4 and the bug check consists predominantly neonates (rather than eggs), YESTA 20B (a dried debittered brewer's yeast, *S. cerevisiae*) and a biological pesticide should be applied to restore the ratio to 0.5 or higher.

If the predator-to-pest ratio is 0.4 or lower following the application of a biological insecticide and the Helicoverpa population is predominantly larvae, a selective insecticide should be used to control the larvae before they develop to mediums. Three days after applying a selective insecticide, re-apply YESTA 20B (a dried debittered brewer's yeast, *S. cerevisiae*) to restore the system.

Figure 6A:
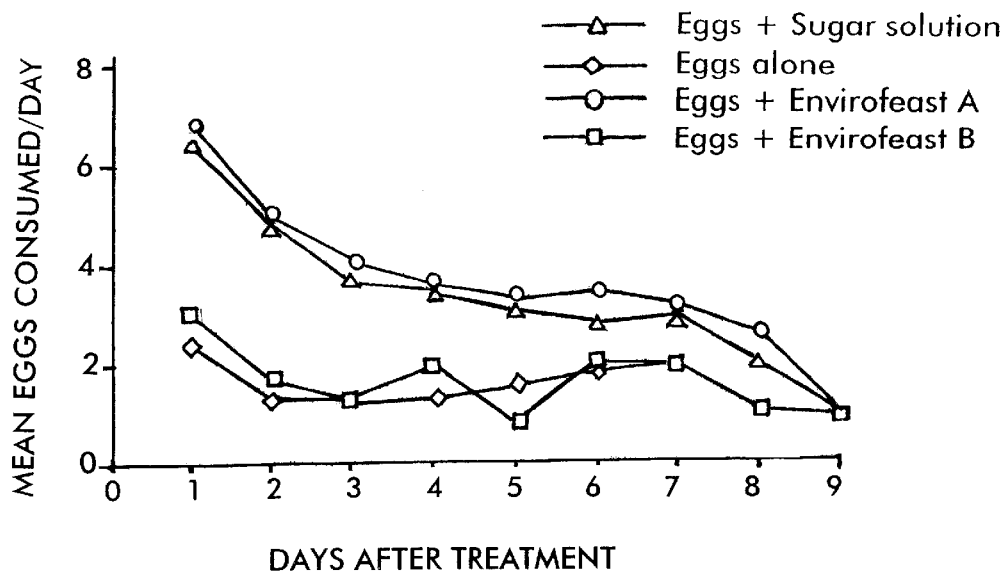
FIGS. 6a and 6b show the effect of the brewer's yeast YESTA 20a (referred to Environfeast A) and YESTA 20B (a dried debittered brewer's yeast, *S. cerevisiae*) (Environfeast B) on the number of Helicoverpa spp. eggs consumed by *C. transversalis*.
Figure 6B:
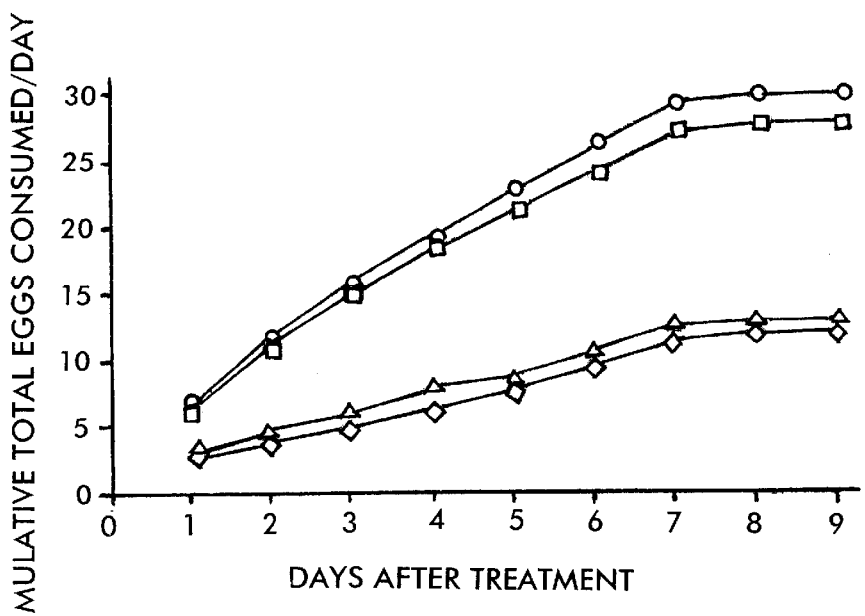

Apart from attracting and arresting predatory insects when applied to cotton crops, the yeast of the present invention can increase the consumption rate of some predators, particularly ladybird beetles (FIGS. 6a and 6b), increase their searching ability and suppress oviposition of Helicoverpa spp. females. This study shows that the number of Helicoverpa spp. eggs consumed by transverse ladybird beetle is significantly higher on cotton leaves treated with the product of the present invention than on leaves treated with a sugar solution or water.

TABLE 1

Ovipositional preferences of *Helicoverpa armigera* (n = 110 pairs) and *H. puntigera* (n = 100 pairs) on cotton plants sprayed with various food supplements in the mesh house at the Agricultural Research Station, Narrabi, November 1992. (Results of free choice tests)

| Treatments | *H. armigera* No. of eggs/plant (n = 40 plants/treatment) | *H. puntigera* No. of eggs/plant (n = 40 plants/treatment) |
|---|---|---|
| 0.06 kg of Brewers yeast in 1 L of water | 11.78 a | 2.10 a |
| 0.07 kg of raw sugar in 1 L of water | 17.10 b | 19.40 b |
| 0.06 kg of Brewers yeast + 0.07 kg of sugar in 1 L of water | 10.78 a | 3.73 a |
| 0.08 g polysaccharide + 7 ml (0.5%) petroleum oil in 1 L of water | 25.20 c | 3.13 a |
| 1 L of water (Control) | 28.50 c | 23.17 b |

Means within a column followed by same letter not significantly different (P > 0.05) (Duncan's Multiple Range Test).

TABLE 2

No choice test for oviposition of *Helicoverpa armigera* (n = 8 pairs) and *H. puntigera* (n = 5) on cotton plants in the mesh house at the Agricultural Research Station, Narrabi, January 1993.

| Treatments | *H. armigera* No. of eggs/plant (n = 40 plants/treatment) | *H. puntigera* No. of eggs/plant (n = 40 plants/treatment) |
|---|---|---|
| 0.06 kg of Brewers yeast in 1 L of water | 1.11 a | 0.37 a |
| 0.07 kg of raw sugar in 1 L of water | 3.82ab | 1.91bc |
| 0.06 kg of Brewers yeast + 0.07 kg of sugar in 1 L of water | 3.61ab | 0.83ab |
| 0.08 g polysaccharide + 7 ml (0.5%) petroleum oil in 1 L of water | 5.33 b | 1.99 c |
| 1 L of water | 7.61 b | 4.45 d |

Means within column followed by same letter not significantly different (P > 0.05) (Duncan's Multiple Range Test).

TABLE 3

Mean numbers of *Helicoverpa armigera* and *H. punctigera* eggs and larvae/metre/sample date on commercial cotton plants sprayed with various food supplements at Norwood (Moree) and Auscott (Narrabi) October 1992 - March 1993

| | Eggs/metre/ sample date | | Larvae/metre/ sample date | |
|---|---|---|---|---|
| Treatments | Norwood | Auscott | Norwood | Auscott |
| 7.20 kg of Brewers yeast in 120 L of water | 1.85 a | 0.36 a | 1.31 a | 0.14 a |
| 8.40 kg sugar in 120 L of water | 2.79ab | 0.89ab | 1.31 a | 0.09 a |
| 7.20 kg Brewers yeast + 8.40 kg sugar in 120 L of water | 2.21 a | 0.43 a | 1.29 a | 0.11 a |
| 9.60 g polysaccharide + 840 ml petroleum oil in 120 L of water | 3.83 b | 0.59ab | 1.71 a | 0.14 a |
| Control (unsprayed) | 6.44c | 1.09b | 2.66 b | 0.21 a |
| Growers plot (treated control) | 6.21c | 2.39c | *0.60 c | 0.27 a |

Means within column followed by same letter not significantly different (P > 0.05) (Duncan's Multiple Range Test).

TABLE 4

Comparison of the final fruit yield per metre (mature + open bolls) on the various food sprayed plots and growers plot receiving conventional control programme at Norwood, March 18, 1993 and Auscott, March 22, 1993. (Mean of 4 replicates per treatment).

| Treatments | Norwood No. of mature bolls/m | Auscott No. of mature bolls/m |
|---|---|---|
| 7.20 kg Brewers yeast in 120 L of water | 93.00 a | 118.50 a |
| 8.40 kg sugar in 120 L of water | 71.25 b | 90.25 b |
| 7.20 kg Brewers yeast + 8.4 kg sugar in 120 L of water | 71.25 b | 93.0 b |
| 9.60 g polysaccharide + 840 ml petroleum oil | 84.75 b | 98.50 b |
| Control (unsprayed) | 75.25 b | 91.00 b |
| Growers plot (treated control) | 99.00 a | 76.25 c |

Means within column followed by same letter not significantly different (P > 0.05) (Duncan's Multiple Range Test).

TABLE 5

Conventional control programme based on current pest thresholds used by Grower during the 1992/92 cotton season.

| Pesticides | Date of Application | Rate | Method of Application |
|---|---|---|---|
| Lorsban | 11-12-92 | 0.6 L/ha | Water injection |
| Temik | " | 3.0 kg/ha | Applicator on planter |
| Endo ULV | 12-11-92 | 3.0 L/ha | By air |
| Dipel ES | " | 3.0 L/ha | Ground rig |
| Endo ULV | 26-11-92 | 3.0 L/ha | By air |
| Dipel ES | 27-11-92 | 3.0 L/ha | Ground rig |
| Endo ULV | 5-12-92 | 3.0 L/ha | By air |
| Rogor | 5-12-92 | 0.5 L/ha | By air |
| Thuricide | 11-12-92 | 2.5 L/ha | By ground rig |
| Larvin | 11-12-92 | 0.5 L/ha | By ground rig |
| Endo EC | 18-12-92 | 2.1 L/ha | By air |
| Larvin 375 | " | 0.5 L/ha | By air |
| Larvin 375 | 30-12-92 | 0.5 L/ha | By air |
| Maverik | 10-1-93 | 3.5 L/ha | By air |
| Endo ULV | 27-1-93 | 3.0 L/ha | By air |
| Bt | 27-1-93 | 2.0 L/ha | By air |
| Bulldock | 9-2-93 | 2.5 L | By air |
| Lannate | 9-2-93 | 1.0 L | By air |
| Thuricide | 18-2-93 | 2.5 L | By air |
| Larvin 375 | 18-2-93 | 0.5 L | By air |
| Talstar | 18-2-93 | 0.8 L | By air |
| Rogor | 11-3-93 | 0.5 L | By air |

TABLE 6

Major predators of cotton pests in Australia.

| Order | Family | Predator Species | Predator Group | pest Species* |
|---|---|---|---|---|
| Coleoptera | Coccirellidae | Coccinella transversalis (Fabricius) | Predatory beetles | Helicoverpa spp. (Cotton bol & bucworm) |
| | | Adalia bipunctata (Linnaeus) | | Earias heugell (Rough bollworm) |
| | Melyridae | Dicranolauis bellutus (Guerin-Meneville) | | Crocidesema plebeiana (cotton tipworm) |
| Hemiptera | Nabidae | Nabis capsitormis (Germar) | Predatory bugs | Pectinophora scutigera (Pink bollworm) |
| | Lygaeidae | Geocoris lubra (kirkaldy) | | Anomis flava (Cotton looper) |
| | Pentatomidae | Cermatulus naselis (Westwood) | | Loxostege affinitaiis (Cotton web-spinner) |
| | | Ocnelia schellenbergil (Guerin-Meneville) | | Agrctis infusa (Bogong moth) |
| | Reduviidae | Coranus triabeatus (Horvath) | | Spodoptera litura (Cluster caterpillar) |
| Neuroptera | Chrysopidae | Chrysopa spp. | Predatory lacewings | Chryssodeixis argentifera (Tobacco looper) |
| Hemerobiidae | | Micromus tasmaniae (Walker) | | Thrips imaginis (plaque thrips) |
| Arareica | Lycosidae | Lycosa spp. | Spiders | Tatranychus urticac (Two spotted mites) |
| | Oxyopidae | Oxyopes spp. | | Apnis gossypii (Cotton aphid) |
| | Salticidae | Salticidae spp. | | Myzus persicac (Green peach aphid) |
| | Araneidae | Araneus spp. | | Creontiades dilutus (Green mirid) |
| | | | | Campylomma livida (Apple dimpling bug) |

*All listed predators feed on eggs and early stage larvae of all listed pest species in cotton.

What is claimed is:

1. A method of controlling an insect pest selected from the group consisting of cotton bollworm, native budworm, plaque thrips, cotton bud thrips, predatory thrips, onion thrips, *Earias huegeli, Crocidosema plebeiana, Pectinophora scutigera, Anomis flava, Loxostege affinitalis, Agrotis infusa, Spodoptera litura, Chryssodeixis argentifera, Tetranychus urticae, Aphis gossypii, Myzus persicae, Creontiades dilutus* and Campylomma livida on a plant, which comprises applying a dried debittered brewer's yeast, S. cerevisiae YESTA 20B, to the plant in an amount sufficient to attract, augment or conserve natural enemies of the insect pest in sufficient numbers to produce a population of the natural enemies able to control the insect pest.

2. The method of claim 1 further comprising applying to the plant an effective amount of a food substance suitable for sustaining the natural enemies.

3. The method of claim 1, wherein the plant is a cotton plant.

4. The method of claim 3, wherein the insect pest is cotton bollworm.

5. The method of claim 3, wherein the insect pest is native budworm.

6. The method of claim 1, wherein the plant is a vegetable plant.

7. The method of claim 1, wherein the plant is a fruit plant.

* * * * *